(12) United States Patent
Aalders

(10) Patent No.: US 11,517,651 B2
(45) Date of Patent: *Dec. 6, 2022

(54) APPARATUS AND METHOD FOR EVACUATING A SYSTEM

(71) Applicant: KONINKLIJKE PHILIPS N.V., Eindhoven (NL)

(72) Inventor: Arnold Aalders, Sprang Capelle (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 578 days.

This patent is subject to a terminal disclaimer.

(21) Appl. No.: 16/565,630

(22) Filed: Sep. 10, 2019

(65) Prior Publication Data

US 2020/0000986 A1    Jan. 2, 2020

Related U.S. Application Data

(63) Continuation of application No. 14/908,266, filed as application No. PCT/EP2014/065574 on Jul. 21, 2014, now Pat. No. 10,449,273.

(30) Foreign Application Priority Data

Jul. 30, 2013 (EP) ..................... 13178576

(51) Int. Cl.
| *A61M 1/06* | (2006.01) |
| *A61M 39/24* | (2006.01) |
| *F04B 23/02* | (2006.01) |
| *F04B 41/02* | (2006.01) |
| *F04B 37/14* | (2006.01) |
| *A61M 1/00* | (2006.01) |

(52) U.S. Cl.
CPC .............. *A61M 1/062* (2014.02); *A61M 1/06* (2013.01); *A61M 39/24* (2013.01); *F04B 23/02* (2013.01);
(Continued)

(58) Field of Classification Search
CPC ...... A61M 1/062; A61M 1/0066; A61M 1/06; A61M 2039/242; A61M 2039/2413;
(Continued)

(56) References Cited

U.S. PATENT DOCUMENTS

| 6,164,242 A | 12/2000 | Olofsson |
| 6,494,163 B1 | 12/2002 | Oort |

(Continued)

FOREIGN PATENT DOCUMENTS

| GB | 2392626 A | 3/2004 |
| WO | 2012127405 A1 | 9/2012 |

*Primary Examiner* — Tasnim Mehjabin Ahmed

(57) ABSTRACT

The present invention relates to an apparatus for evacuating a collection container, comprising a pump, the pump being suitable for being in connection with the collection container with its inlet, a pressure tank and a directional control valve, the pump transporting a medium out of the collection container and the pressure tank into the atmosphere when the pressure tank is connected to its inlet, wherein the directional control valve is configured to switch the pressure tank from the inlet to the outlet of the pump when a predefined criterion is fulfilled. The present invention further relates to a breast pump device comprising an apparatus for evacuating a collection container and a receiving funnel for receiving a beast of a woman.

26 Claims, 4 Drawing Sheets

(52) U.S. Cl.
CPC .............. *F04B 37/14* (2013.01); *F04B 41/02* (2013.01); *A61M 1/80* (2021.05); *A61M 2205/3337* (2013.01); *A61M 2205/3351* (2013.01)

(58) Field of Classification Search
CPC .... A61M 2205/3337; A61M 2205/3351; A61J 5/007; A61J 5/04; F04B 23/02; F04B 37/14
See application file for complete search history.

(56) References Cited

U.S. PATENT DOCUMENTS

| | | | |
|---|---|---|---|
| 6,840,918 B1 | 1/2005 | Britto | |
| 8,001,930 B2 | 8/2011 | Bosma | |
| 8,137,305 B2 | 3/2012 | Kelly | |
| 10,449,273 B2 * | 10/2019 | Aalders | .................. F04B 37/14 |
| 2003/0073951 A1 * | 4/2003 | Morton | .............. A61B 10/0041 604/73 |
| 2003/0236491 A1 | 12/2003 | McKendry | |
| 2004/0087898 A1 * | 5/2004 | Weniger | ................ A61M 1/064 604/74 |
| 2005/0283112 A1 * | 12/2005 | Britto | ...................... A61M 1/06 604/74 |
| 2009/0099511 A1 * | 4/2009 | Sutrina | .................. A61M 1/74 604/74 |
| 2010/0075285 A1 | 3/2010 | Stalling | |
| 2011/0098639 A1 | 4/2011 | Kirchner | |
| 2013/0016852 A1 | 1/2013 | Regunathan | |

* cited by examiner

APPARATUS AND METHOD FOR EVACUATING A SYSTEM

CROSS-REFERENCE TO PRIOR APPLICATIONS

This application claims the benefit or priority of and describes relationships between the following applications: wherein this application is a continuation of U.S. patent application Ser. No. 14/908,266, filed Jan. 28, 2016 which is the National Stage of International Application No. PCT/EP2014/065574, filed Jul. 21, 2014, which claims the benefit of European Application No. 13178576.8 filed on Jul. 30, 2013. These applications are hereby incorporated by reference herein.

FIELD OF THE INVENTION

The present invention relates to an apparatus for evacuating a system, a breast pump device and a method for controlling a breast pump device.

BACKGROUND OF THE INVENTION

Numerous applications require vacuum pumps to deliver (partial) vacuum for use in different industrial, scientific and medical processes. These different processes require different levels of vacuum leading to a range of different pump types and pumping principles. Two main parameters of a vacuum pump are the achievable flow and the achievable vacuum level, i.e. pressure level. Every pumping principle has its specific benefits and downsides, and every application has its specific requirements for the pump. Usually a pump being able to provide a higher level of vacuum or a higher flow is larger and more difficult to manufacture. Thus, a compromise between required flow, maximum vacuum level, manufacturing costs, construction size and other parameters has to be found when choosing or manufacturing a vacuum pump for a specific application.

One application area for vacuum pumps is the field of breast pump devices, i.e. devices for extracting milk from the breast of a lactating woman. Such devices usually include a vacuum pump for delivering a (partial) vacuum, which is applied to the breast of a woman in order to suck milk out of the breast. WO 2012/127405 A1 discloses a breast pump device operable to generate a negative pressure. The maximum negative pressure that can be applied by a breast pump device is a function of the maximum pressure value that the used (partial) vacuum pump can provide. If a higher level of vacuum is required, a different type of pump is required usually making the breast pump device larger and/or more expensive to manufacture.

In US 2005/0283112 A1 a breast pump is presented. The device includes a breast shield adapted to fit over a nipple of a breast and a flow line coupled to the breast shield. The flow line is adapted to allow air to flow there through a pump coupled to the breast shield via the flow line. The pump includes a pump intake and a pump exhaust and is operable to create a pressure drop between the nipple and the pump, wherein the pressure drop creates a suction at the breast shield by lowering the pressure of air in the flow line. A blow-back valve is disposed between the flow line and the pump and has a valve piston disposed in a valve housing The valve housing includes a flow line aperture that communicates via the flow line with the breast shield, a valve inlet adapted to communicate external to the flow line, and a valve exhaust adapted to communicate external to the flow line. The valve piston is adapted to alternatively seal the valve inlet and the valve exhaust.

In US 2013/0165852 A1 an electric breast milk pump is presented. The pump has an electric motor, a pump driven by the motor, a suction cup, an electrically activated first three-way valve in a suction line, an electrically activated second three-way valve in a pressure line, an electronic control system, which sets the electric motor into an operating mode or an idle mode depending on an activation of a switch. In the operating mode, it operates the electric motor and the electrically activated first and second three-way valves in cycles, which comprise a suction phase, in which the electric motor is switched on, the inlet of the pump is connected to the suction cup via the first three-way valve and a floater valve, the pump outlet is connected via the second three-way valve.

SUMMARY OF THE INVENTION

It is an object of the present invention to provide an apparatus for evacuating a system and delivering an adequate vacuum level albeit allowing for cost-effective manufacturing and implementation in a small housing. It is further an object of the present invention to provide and a breast pump device and a method for controlling a breast pump device.

In a first aspect of the present invention there is provided an apparatus for evacuating a system, comprising a pump for generating a decrease of pressure between its inlet and its outlet, the pump being suitable for being in connection with the system with its inlet, a pressure tank for preserving an applied pressure value and a directional control valve for switching the pressure tank to either the inlet or the outlet of the pump, the pump transporting a medium out of the system and the pressure tank into an ambience when the pressure tank is connected to its inlet, wherein the directional control valve is configured to switch the pressure tank from the inlet to the outlet of the pump when a predefined criterion is fulfilled.

In a further aspect of the present invention there is provided a breast pump device comprising an apparatus as described above and a system including a receiving funnel for receiving a breast of a woman and a milk reservoir for collecting milk.

In yet another aspect of the present invention, there is provided a method for controlling a breast pump device, comprising configuring a pump for generating a decrease of pressure in a system and in a pressure tank, the pump transporting a medium out of the system and the pressure tank into an ambience when the pressure tank is connected to its inlet, determining whether a predefined criterion is fulfilled, configuring a directional control valve to switch the pressure tank from the inlet to the outlet of the pump when said predefined criterion is fulfilled.

Preferred embodiments of the invention are defined in the dependent claims. It shall be understood that the claimed method and breast pump device have similar and/or identical preferred embodiments as the claimed apparatus and as defined in the dependent claims.

The apparatus according to the present invention allows increasing the achieved vacuum level by making use of a directional control valve as well as an additional pressure tank. The pump transports a medium from an inlet side to an outlet side and thereby generates a pressure decrease between the two sides. The transported medium can thereby include any kind of fluid, i.e. gas or a liquid, which, when transported out of the system by means of the pump, induces a pressure decrease in the system. If the outlet of the pump is connected to the ambience such that the transported medium is released to the ambience the pressure in the system decreases in comparison to the pressure in the ambience.

According to the present invention, the pump not only transports the medium from the system but also the medium comprised in the pressure tank to its outlet such that both the pressure in the system as well as the pressure in the pressure tank decrease. Thus, both the system and the pressure tank are sucked out by the pump.

The pressure tank (also called vacuum tank) thereby allows preserving an applied (low) pressure value by providing a constant volume, which is not changed in spite of varying pressure values on the inside and outside of the tank. A possible embodiment of such a pressure tank can, e.g., be a stiff, airtight and inflexible metal corpus with a single opening to be connected to the pump. Further, in this context, preserving an applied pressure value refers to applying or inducing a pressure value, e.g. by sucking a medium out of the pressure tank, and then closing or sealing the opening of the pressure tank such that the pressure inside the pressure tank remains constant until a pressure compensation is performed, e.g. by unclosing the opening and releasing the medium in the tank to the ambience or letting a medium from the ambience into the tank.

Alternatively to changing the pressure inside the pressure tank by pumping a medium into or out of the tank, it is also possible to (passively) let the pressure tank adapt to a pressure level, i.e. a pressure value, and then transport it to an area where the surrounding pressure is different, such that the pressure condition of the initial environment is preserved. The pressure tank can be used in both directions, i.e. can either preserve an underpressure or an overpressure in relation to the ambience.

According to the present invention, the pressure tank is connected to the inlet or to the outlet of the pump by means of a directional control valve. Such a directional control valve allows switching different paths so that a medium can be guided to different ports depending on the setting of the directional control valve. According to the present invention the directional control valve particularly provides the functionality of switching the pressure tank to the inlet of the pump in a first setting or to the outlet of the pump in a second setting. Thus, it is possible to connect the opening of the pressure tank to either side of the pump.

Further, according to the present invention the directional control valve performs such a switching procedure, i.e. switches the pressure tank from one side of the pump to the other, when a predefined criterion is fulfilled. For instance, the pressure tank is initially connected to the inlet of the pump such that the pump, apart from sucking a medium out of the system also sucks a medium out of the pressure tank. Then, as soon as a predefined criterion is met, the pressure tank is connected to the outlet of the pump. In this configuration, when the directional control valve is in its first setting, the pump transports the medium out of the system and the pressure tank into the ambience. Then, after the switching of the directional control valve to its second setting, the medium is transported from the system at the pump's inlet into the pressure tank at the pump's outlet.

One advantage of the apparatus according to the present invention is that the generated decrease or overall-decrease of pressure is boosted. Initially, the pump generates a certain decrease of pressure between the ambience and the system and the pressure tank. As soon as the predefined criterion is fulfilled, i.e. the pressure level cannot be decreased any further, the pressure tank is switched to the outlet of the pump by means of the directional control valve. Directly after switching, this results in equilibrium of pressures on the inlet and outlet of the pump. Then, it is exploited that the pump can generate an even lower pressure in the system compared to the ambience if the pressure level at the outlet of the pump is already lower than the pressure level in the ambience. Independent from the pressure level in the ambience the pump generates a decrease of pressure between its inlet and its outlet. Thus, if the pressure level at its outlet is already lower than the pressure level in the ambience it is possible to further decrease the pressure level at the inlet of the pump. This is exploited by the present invention by means of a directional control valve which can switch the pressure tank from the inlet to the outlet of the pump when a predefined criterion is fulfilled. In particular, the achievable pressure level or vacuum level of the pump is improved by switching the pressure tank as outlined above. The achievable vacuum level, i.e. the lowest possible pressure that can be generated with the pump, is boosted in comparison to the originally achievable vacuum level.

In a first embodiment of the present invention the apparatus additionally comprises a unidirectional valve coupled between the outlet of the pump and the pressure tank for preventing a backflow of fluid from the ambience into the pump and/or the pressure tank. A unidirectional valve basically allows a medium to pass in one direction but prevents the medium from passing in the other direction. According to the first embodiment of the present invention, this unidirectional control valve is arranged at the outlet of the pump. Thus, even if the pressure tank is connected to the outlet of the pump by means of the directional control valve, a backflow of the transported medium from the ambience into the pressure tank or into the pump is prevented. Initially, as long as the pressure tank is connected to the inlet of the pump, the unidirectional valve just seals the outlet of the pump from the ambience and allows the medium transported by the pump to escape into the ambience. However, no medium can flow back into the pump or into the system from the ambience against the direction of the unidirectional valve. Then, as soon as the pressure tank is switched from the inlet to the outlet of the pump as described above, the unidirectional valve also prevents any medium from flowing back from the ambience into the pressure tank. In this configuration the outlet of the pump and the pressure tank are unidirectionally separated from the ambience. One advantage of this unidirectional valve is that the pressure can be preserved in comparison to the pressure in the ambience.

According to a further embodiment of the present invention the apparatus comprises a sensor for determining the pressure in the pressure tank. This pressure sensor can, e.g., be based on a capacitive, electromagnetic, piezoelectric or piezoresistive measurement principle and can provide information on the pressure of the medium or fluid in the pressure tank. The sensor can be a smart sensor providing a digital and corrected output signal comprising information on the absolute pressure in the pressure tank or an analog sensor providing an analog reading of a signal being dependent on the pressure in the pressure tank. The signal generated by the sensors allows controlling the apparatus according to the present invention, e.g. by allowing the use of a close-loop control, wherein a specific parameter of the apparatus is directly configured based on the obtained sensor signal.

One example of the use of this sensor is further detailed in in another embodiment of the present invention, wherein the directional control valve is configured to switch the pressure tank from the inlet to the outlet of the pump when the pressure in the pressure tank is below a predefined pressure threshold. Thus, the pressure in the pressure tank determined by the above-described sensor is used as a criterion for determining when the switching of the pressure tank from the inlet to the outlet of the pump is to be performed. By defining a specific pressure threshold level, i.e. a predefined threshold, the configuration of the directional control valve can be directly linked to the current pressure in the pressure tank being equivalent to the pressure in the system while the pressure tank is connected to the inlet of the pump. This predefined threshold can be chosen depending on the characteristics of the pump, e.g. the maximum achievable pressure difference or the maximum vacuum level. Depending on the chosen setting, one advantage of this embodiment is that the control of the switching process becomes simple and can be realized easily.

Further, according to another embodiment of the present invention, the apparatus further comprises a sensor for determining the throughput of the pump. Such a throughput sensor could, e.g., be a flow sensor realized as one or multiple pressure sensors, a thermal flow meter, a mechanical positive displacement meter or any other flow sensor or flow meter. This flow sensor can basically be used as an alternative to the above described sensor for determining the pressure on the pressure tank. A comparable functionality can be realized. Preferably, the use of such a sensor for determining the throughput of the pump also allows automatically triggering the switching procedure without requiring further user input.

In a preferable embodiment of the present invention the directional control valve is configured to switch the pressure tank from the inlet to the outlet of the pump when the throughput of the pump exceeds a predefined throughput threshold. As described above, the reading of this sensor for determining the throughput of the pump is evaluated and the obtained sensor value used as a criterion for determining whether the pressure tank is to be switched from the inlet to the outlet of the pump. In particular, this principle can be used if the threshold value, i.e. the throughput value at which the switching is to take place, is determined based on the characteristics of the pump. One possible setting of this threshold value can, e.g., be a certain percentage of the maximum throughput that can be realized with the pump. Thus, as soon as the pump works at a comparably low efficiency, the pressure tank is switched from the inlet to the outlet and the throughput of the pump is increased. As soon as the maximum total pressure decrease is reached, the sensor will again register only a small flow.

In another embodiment of the present invention the apparatus further comprises a release valve for releasing the pressure from the system and/or from the pressure tank to the ambience. In some applications it is necessary to be able to release the pressure or, in particular, the vacuum from the system to the ambience in order to continue with the intended application. Such a release valve could be operated electrically or manually and may be realized in form of a simple butterfly valve or any other type of valve. Depending on the attaching point of this release valve it is possible to release the pressure from the system and the pressure tank or from the system alone, e.g. if the pressure tank is currently connected to the outlet of the pump. The release valve is thereby preferably operated automatically and without a need for any external input except the pressure difference between the system or the pressure tank and the ambience. The release valve can then function as a safety valve preventing the system or the tank from a too low/high pressure in case of a malfunctioning or an uncontrolled behavior of the pump. If, e.g., the evacuated system is a milk reservoir of a breast pump device, such a safety valve can prevent the user from harm.

The apparatus for evacuating a system according to the present invention may further comprise a (optionally adjustable) flow restrictor for controlling the flow of the transported medium from the pressure tank to the outlet of the pump. Such a flow restrictor allows for a smoother and/or gentler pump curve, in particular by allowing a limiting of the maximum throughput.

In a preferred embodiment of the present invention the pump is a positive displacement vacuum pump for moving a fluid, in particular gas, from its inlet to its outlet. This pump can either be an electric or a mechanical pump powered by hand and/or foot movements of a person in different embodiments of the present invention. Depending on the application the different types of pumps have their advantages and disadvantages. Particularly if gas, i.e. gas molecules, are to be pumped from the inlet to the outlet of the pump a positive displacement vacuum pump is advantageous. Such a positive displacement vacuum pump relies on the expansion of a given volume whereby a pressure in the expanded volume is decreased. Then, a part of the volume is separated and expanded again. This procedure can be repeated several times increasing the level of vacuum and can be easily implemented when pumping gas. The main concern is then the vacuum level, i.e. the minimum number of remaining molecules per volume, the pump can generate. One advantage of such positive displacement vacuum pumps is their simple construction and broad market availability.

No matter which pumping principle is used the pump comprised in the apparatus can be an electric pump powered by battery or mains-powered, which could, e.g., be controlled by a processor device or provide a direct user interface. Alternatively, it is further possible that the apparatus comprises a mechanical pump that does not require any electric energy but can be powered by manual power conversion, e.g. by hand and/or foot movements of a person. One possibility for such a mechanical pump is the use of a handle that is periodically agitated and that sets a pumping mechanics, e.g. the above-described positive displacement principle, into motion. Advantages of a mechanical pump include that it is not necessary to charge a battery or make use of a cable connection. Also the risk for malfunctioning and possible harm to a user, e.g. in case of a breast pump device, is reduced. An electrical pump on the other hand can be more convenient to use.

In another preferred embodiment of the present invention the directional control valve and the unidirectional valve are combined in a smart valve. Such a smart valve could be an integrated part that combines the functionalities of the control valve and the unidirectional valve in one component. One advantage of combining the two valves in one component is that the construction space can be reduced. It might further be possible to reduce the costs if the number of components in the apparatus is minimized. Such a smart valve can also include the release valve, thus further reducing the number of components. It is further possible that the functions of a safety valve, i.e. the protection of a user of the apparatus or of the apparatus itself, are incorporated in the smart valve. Such a smart valve can be fully mechanically controlled and function based on pressure differences and their mechanical exploitation, i.e. a certain pressure difference causes a material to be deformed and a pressure to be released to the ambience. The smart valve may also include a flow restrictor, which may be adjustable, for controlling the flow between the pressure tank and the pump.

In another embodiment the directional control valve is a 3/2 valve having three ports and two switching positions. Such a 3/2 valve is basically a standard component providing the functionalities required for the switching of the pressure tank from the inlet to the outlet of the pump. The advantage of the 3/2 valve is that the functionality of switching the pressure tank from the inlet to the outlet of the pump can be realized in one single part. Again, this 3/2 valve can function mechanically upon pressure changes or electrically by means of a switching procedure triggered, e.g., by a controller device or by user input.

According to one embodiment of the present invention the directional control valve can be an electrically or mechanically operated valve. If it is an electric valve it becomes possible to use a processor to control the pump and to automate the switching process. Alternatively, the directional control valve can also be mechanically operated. In this case, e.g., a mechanical construction can be used for triggering the switching of the directional control valve from one position to another as soon as the pressure reaches or passes the specified threshold. Also a mechanical operation can be foreseen that allows an operator to manually switch the pressure tank from the inlet to the outlet of the pump.

In another embodiment of the present invention, the apparatus further comprises a controller for controlling the pump and/or the directional control valve. Such a controller could, e.g., be a microcontroller device programmed to perform the required functions. This controller can be used to control the different valves and/or all other components and their interaction in an apparatus according to the present invention or in a device comprising such an apparatus. One advantage of such a controller is that it may also be used for performing other control operations in a breast pump device.

In a further aspect of the present invention there is provided a breast pump device comprising an apparatus for evacuating a system as described above and a system including a receiving funnel for receiving a breast of a woman and a milk reservoir for collecting milk. Such a breast pump device can be used to collect breast milk of a lactating woman in a container, i.e. a milk reservoir. According to this aspect of the present invention the apparatus for evacuating a system evacuates a container which is air tightly connected to the breast of a woman. This container functions as a milk reservoir to collect milk from the lactating woman sucked out of the breast by means of the vacuum generated with the apparatus according to the present invention. The airtight connection of the container with the breast is usually achieved by means of a funnel or a funnel-shaped part, e.g. made of a plastic material, for accommodating the breast of the woman. It is also possible to use an exchangeable funnel to accommodate differently shaped breasts depending on the requirements of an individual user.

According to yet another aspect of the present invention there is provided a method for controlling a breast pump device as described above. Depending on the design of the breast pump device, the pump, the different valves and/or the different sensors may be controlled by at least one controller performing a method for controlling a breast pump. Such a controller may be a microprocessor or a digital signal processor suitable for performing the necessary calculations and control operations. The controller may be connected to the respective valves, the devices and/or the sensors of an apparatus according to the present invention. The method for controlling a breast pump device according to the present invention might correspond to a closed-loop control where the determined settings are directly related to the sensor values or might also correspond to an open-loop control including user feedback. One advantage of such a method is that all functionality of an apparatus according to the present invention or of a breast pump device can be appropriately controlled and/or performed automatically. No or only little user input is necessary to perform the different control steps.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
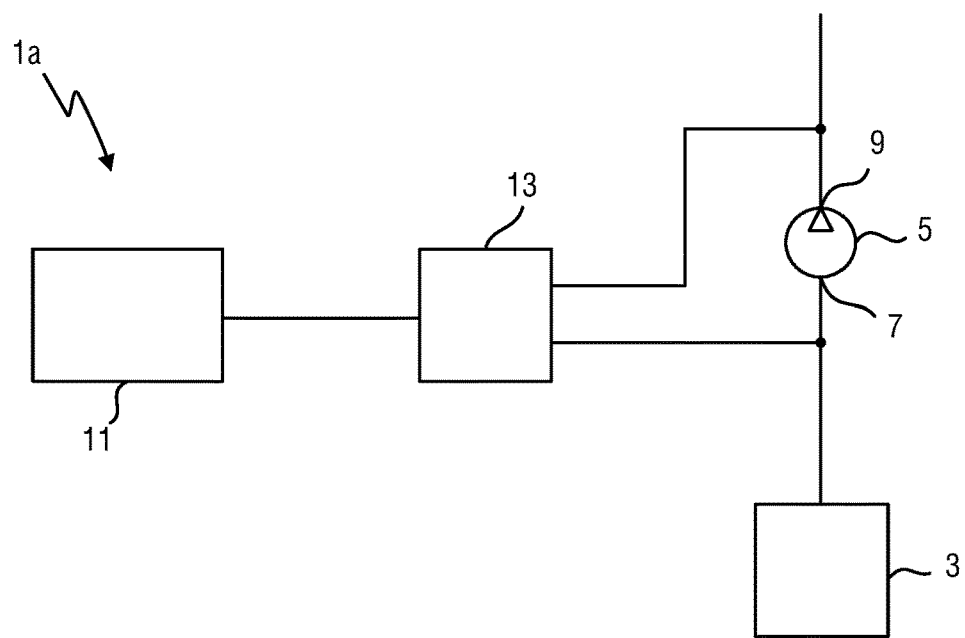
FIG. 1 shows a schematic illustration of a first embodiment of the present invention.

In FIG. 1 an apparatus 1a for evacuating a system according to a first embodiment of the present invention is schematically illustrated. The apparatus 1a comprises a pump 5 which generates a decrease of pressure between its inlet 7 and its outlet 9 and which is connected to the system 3 with its inlet 7. The pump 5 thus transports a medium from its inlet 7 to its outlet 9 and thereby generates a decrease of pressure. The apparatus 1a further comprises a pressure tank 11 which allows preserving an applied pressure value for a period of time. Further, there is comprised a directional control valve 13 for switching the pressure tank 11 to either the inlet 7 or the outlet 9 of the pump 5. In order to provide the functionality according to the present invention, i.e. to allow generating a higher level of vacuum in comparison with the use of the pump 5 alone, the directional control valve 13 is configured to switch the pressure tank 11 from the inlet 7 to the outlet 9 of the pump 5 when a predefined criterion is fulfilled. The directional control valve 13 therefore provides different connection ports, i.e. openings, which allow the intake of a medium and which can be switched together in different configurations.

In the illustrated embodiment of the present invention the directional control valve 13 particularly has three ports. These three ports can be switched such that either the inlet of the pump 7 or the outlet of the pump 9 is coupled to the pressure tank 11. In this context coupled refers to connected such that a medium can flow from one port of the directional control valve 13 to another, depending on the current setting of the directional control valve 13. In order to provide this switching functionality, a directional control valve may, i.e., comprise a spool inside a cylinder which is mechanically or electrically moved from one position to another and thereby allows a medium to flow through one path or another.

As outlined above, the apparatus according to the present invention allows achieving a higher level of vacuum in comparison to the use of the pump 5 alone. Usually, the pump 5 is characterized by the maximum achievable decrease of pressure that it can generate between its inlet 7 and its outlet 9. Thus, if already a lower pressure value is applied at the outlet 9 of the pump 5 the maximum achievable pressure level at the inlet of the pump 5 is higher than if the outlet 9 of the pump 5 is directly connected to the ambience. This behavior is exploited by means of the present invention. Initially, both the system 3 and the pressure tank 11 are sucked out by the pump 5 such that the same level of vacuum (pressure level) is generated in both the system 3 and the pressure tank 11. Then, the pressure tank 11 is switched from the inlet 7 of the pump 5 to the outlet 9 of the pump 5 by means of the directional control valve 13. This allows generating an even higher vacuum level (lower pressure) in the system 3 compared to using the pump 5 alone.

Figure 2:
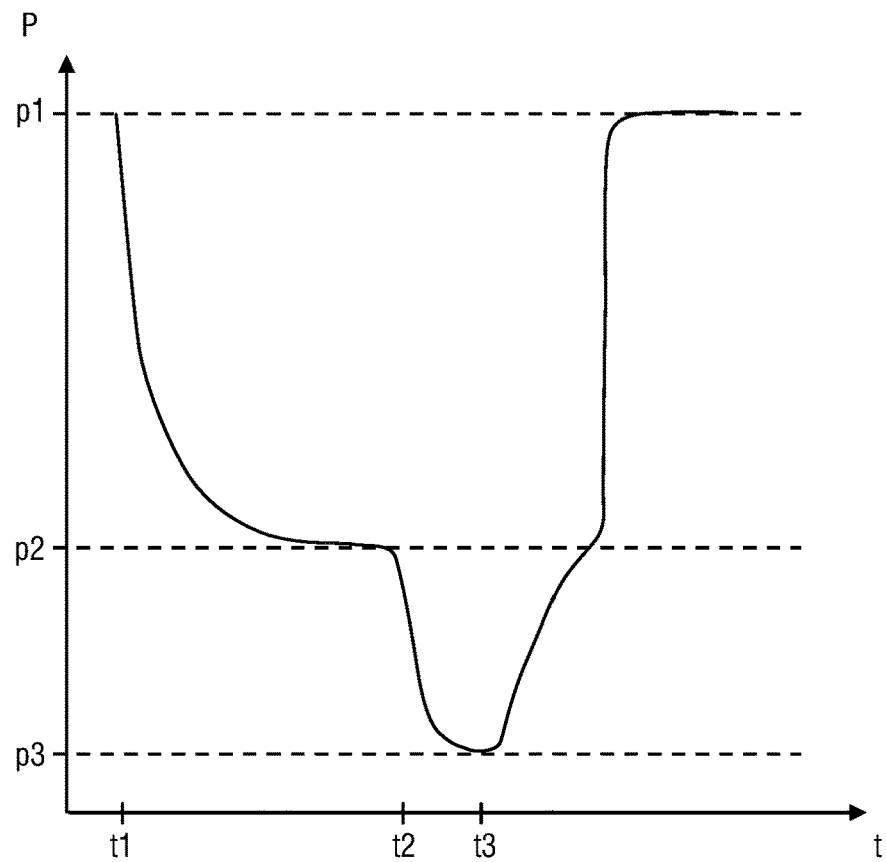
FIG. 2 shows an example for a pressure decrease in a system as generated with the present invention.

FIG. 2 illustrates a typical pressure decrease generated with an apparatus according to the present invention. The pressure p is illustrated as a function of the time t. Initially, the pressure in the system 3 and in the pressure tank 11 are in equilibrium with the pressure in the ambience p1. Then, the pump 5 is switched on t1 and generates a decrease of pressure in both the system 3 and the pressure tank 11. At a certain point in time t2, the maximum achievable vacuum level p2 in this configuration is reached. Due to its construction parameters, the pump 5 is not able to generate a higher level of vacuum (lower pressure). As soon as a predefined criterion is fulfilled, the directional control valve 13 switches the pressure tank 11 from the inlet 7 to the outlet 9 of the pump 5. This predefined criterion can, e.g., be a pressure threshold. By this switching the pressure level at the inlet 7 and the outlet 9 of the pump are temporarily balanced again. The pump 5 can then generate an even higher level of vacuum (i.e. a lower pressure) in the system 3. However, also in this configuration, the pump 5 runs into saturation when a certain pressure value p3 is reached in the system 3. In FIG. 2 the pump 5 is switched off and/or a release valve is opened at t3 leading to a pressure equalization with the ambience.

Figure 3:
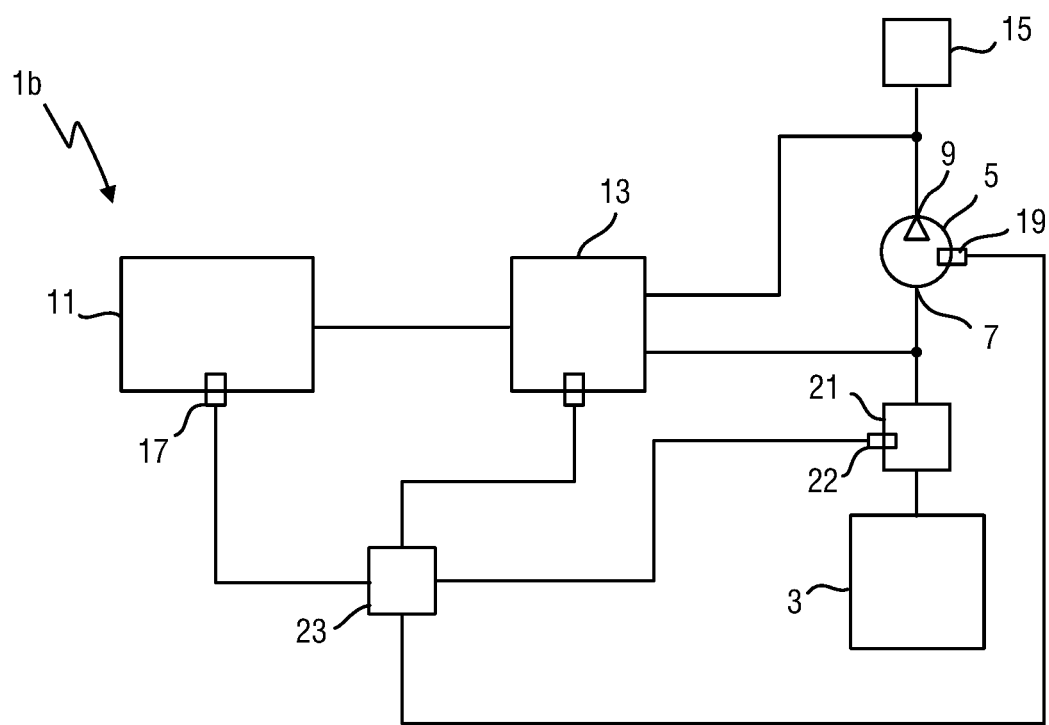
FIG. 3 shows a schematic illustration of another embodiment of the present invention.

FIG. 3 illustrates another embodiment of an apparatus 1b according to the present invention. Compared to the apparatus 1a shown in FIG. 1, there is further comprised a unidirectional valve 15 coupled to the outlet 9 of the pump 5 and to the pressure tank 11. This unidirectional valve 15 can prevent a backflow of the transported medium or any kind of fluid from the ambience into the pump 5 and/or into the pressure tank 11. There is further illustrated a first sensor 17 for determining the pressure in the pressure tank 11. This first sensor 17 allows performing the switching of the pressure tank 11 from the inlet 7 to the outlet 9 of the pump 5 as soon as the pressure in the pressure tank 11 is below a predefined threshold, i.e. a pressure threshold. Still further, the illustrated embodiment shows a second sensor 19 for determining the throughput of the pump 5. This second sensor 19 can be used alternatively or in combination with the sensor 17 to initiate the switching of the directional control valve 13. One obvious possibility is to determine the throughput by means of the throughput sensor 19 and to continuously determine whether the throughput is below a predefined threshold, i.e. the pump 5 only transports a small amount of fluid indicating that the pump 5 is more or less in a saturation state as described above.

FIG. 3 further illustrates a release valve 21 for releasing a pressure from the system 3 and/or the pressure tank 11 to the ambience. This release valve 21 might comprise a control connection 22 allowing a remote control.

Still further, FIG. 3 illustrates a controller 23 for controlling the pump 5, the directional control valve 13, the sensors 17 and 19 and the release valve 21 through its control connection 22. In yet further embodiments of an apparatus according to the present invention the controller 23 might also control other sensors or other electronically controllable components. In particular, the pump 5 can be an electric pump or a mechanical pump requiring specific control pulses or other signals generated by the controller 23.

The controller may also be a combined controller also controlling other functionalities of a breast pump device according to another aspect of the present invention such as allowing a variation of the sucking cycle or the applied pressure in response to user feedback, automatically interrupting the functionality in response to a signal or user input or other functionalities.

Figure 4:
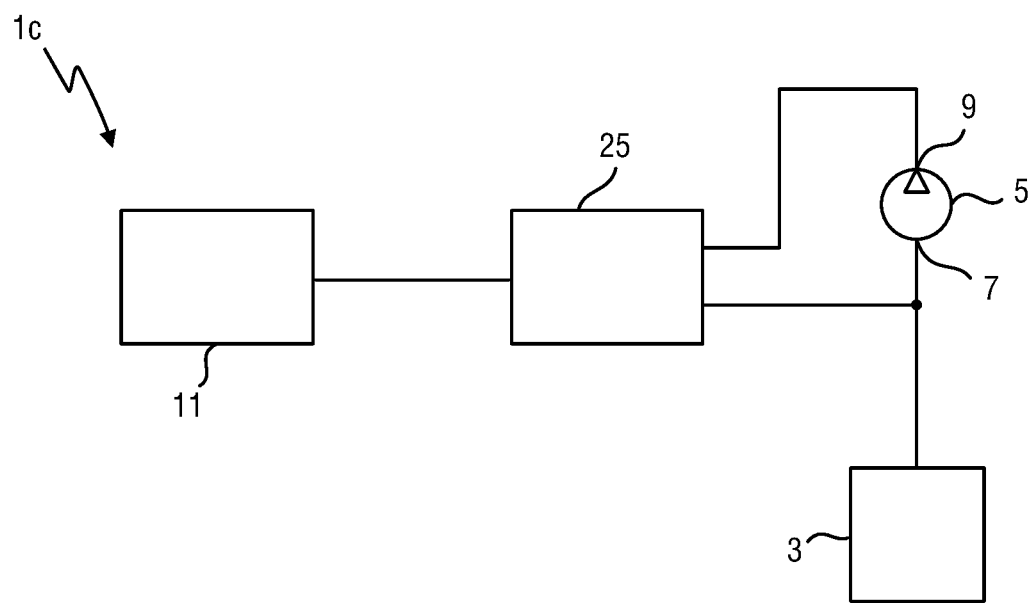
FIG. 4 shows a schematic illustration of a further embodiment of the present invention.

Yet another embodiment of an apparatus 1c according to the present invention is schematically illustrated in FIG. 4. In this embodiment, the apparatus 1c comprises a smart valve 25 combining the functionalities of the directional control valve 13, the unidirectional valve 15 and the release valve 21. This smart valve 25 is connected to the inlet 7 and the outlet 9 of the pump 5, as well as to the pressure tank 11. One main advantage of using a smart valve 25 for providing the different required functionalities is that only one part is needed instead of multiple parts. This can allow for cheaper implementation of an apparatus according to the present invention. Further, failure rate might be reduced with such an integrated part. The smart valve 25 can further include a flow restrictor for speed control.

Figure 5:
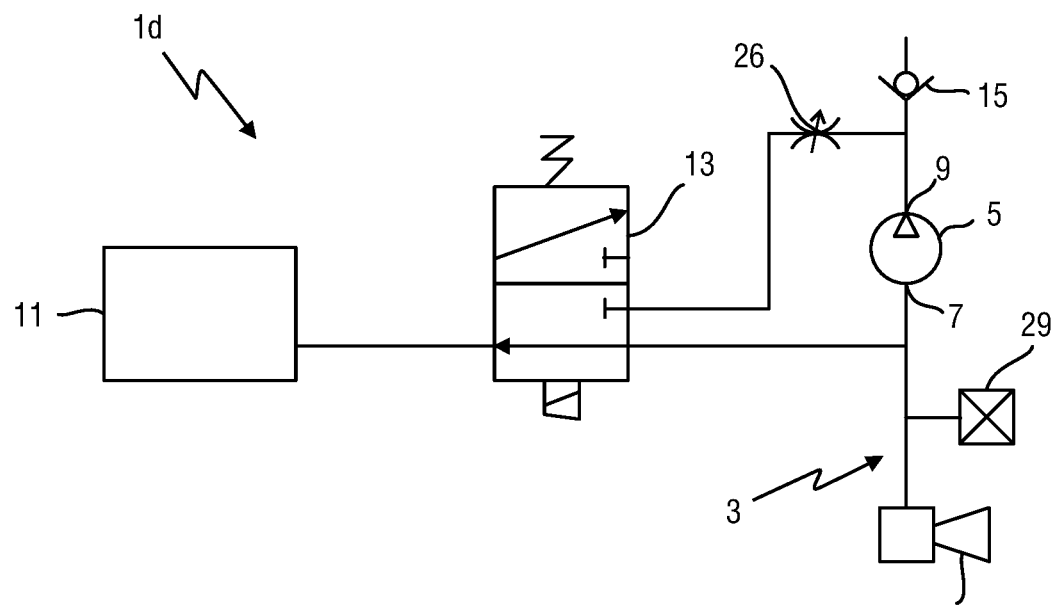
FIG. 5 shows an alternative illustration of an apparatus according to the present invention.

In FIG. 5 yet another schematic illustration of an embodiment of an apparatus 1d according to the present invention is shown. The directional control valve 13 is illustrated and further detailed for highlighting the different parts and possible switching positions. Such a 3/2 valve, i.e. a three way two positions directional control valve, provides the required functionality for switching the pressure tank 11 from the inlet 7 to the outlet 9 of the pump 5. Further, an adjustable flow restrictor 26 is arranged in this embodiment between the directional control valve and outlet 9 of the pump 5. This adjustable flow restrictor allows controlling the flow of the transported medium, in particular by adjustably limiting the maximum throughput.

In this embodiment the system 3 to be evacuated comprises a funnel 27 and a milk reservoir 29. The funnel 27 accommodates a breast of a woman. The partial vacuum generated by the pump 5 is then directly applied to the breast and milk can be extracted. The extracted milk is collected in the reservoir 29. Further, there is illustrated a unidirectional valve 15 to prevent the backflow of a fluid from the ambience into the directional control valve 13 or the pump 5. In particular, in the present embodiment the pump 5 transports air out of the reservoir 29 and releases it into the ambience through the directional valve 15.

Figure 6:
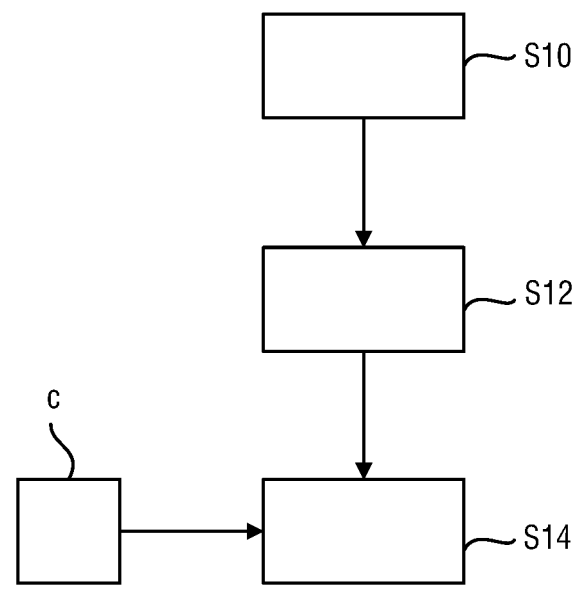
FIG. 6 illustrates a method for controlling a breast pump device.

In FIG. 6 there is illustrated a method for controlling a breast pump device according to an embodiment of an aspect of the present invention. Such a method may, e.g., be performed by a controller included in a breast pump device as described above. The controller may control the different components (e.g. the valves, the sensors, the pump or others) in order to achieve a higher vacuum level (i.e. a lower pressure).

According to the illustrated embodiment in FIG. 6, a pump is initially configured (SW) to generate a decrease of pressure in a system and in a pressure tank. Depending on the type of pump and the type of connection to the controller, this configuration particularly consists in activating the pump. If, e.g., the pump can be operated at different levels, this configuration may also include selecting the appropriate level. Then, it is determined (S12) whether a predefined criterion is fulfilled. Preferably, this determination is based on sensor values obtained from at least one sensor, in particular a pressure sensor or a throughput sensor. Determining whether a predefined criterion is fulfilled thus includes obtaining sensor values from a sensor (i.e. a throughput or pressure sensor). It may then be determined based on said sensor values possibly in combination with user input, whether this predefined criterion is fulfilled. The method for controlling a breast pump according to the present invention further comprises switching (S14) a directional control valve to connect the pressure tank to the outlet of the pump (the pressure tank having initially been connected to the inlet of the pump) when said predefined criterion is fulfilled. For instance, the switching is performed when a certain threshold is exceeded by the sensor value. Switching the directional control valve thereby refers to applying the necessary control signals (c) to the connection cables to trigger a switching procedure. The method for controlling a breast pump device might further comprise (not illustrated) determining control settings for further valves (e.g. directional control valves and/or unidirectional valves) and devices (e.g. a pump) and configuring the valves and the devices based on the determined control settings. Again, configuring in particular refers to applying the necessary control signals to the connection cables (or transmitting the signals via a wireless connection). The method can thereby represent a closed-loop control or an open-loop control as outlined above.

Further, a method (not illustrated) for evacuating a system according to the present invention may comprise generating a decrease of pressure in a system and in a pressure tank, preserving an applied pressure value in the pressure tank and switching the pressure tank from the inlet to the outlet of the pump when a predefined criterion is fulfilled.

Figure 7:
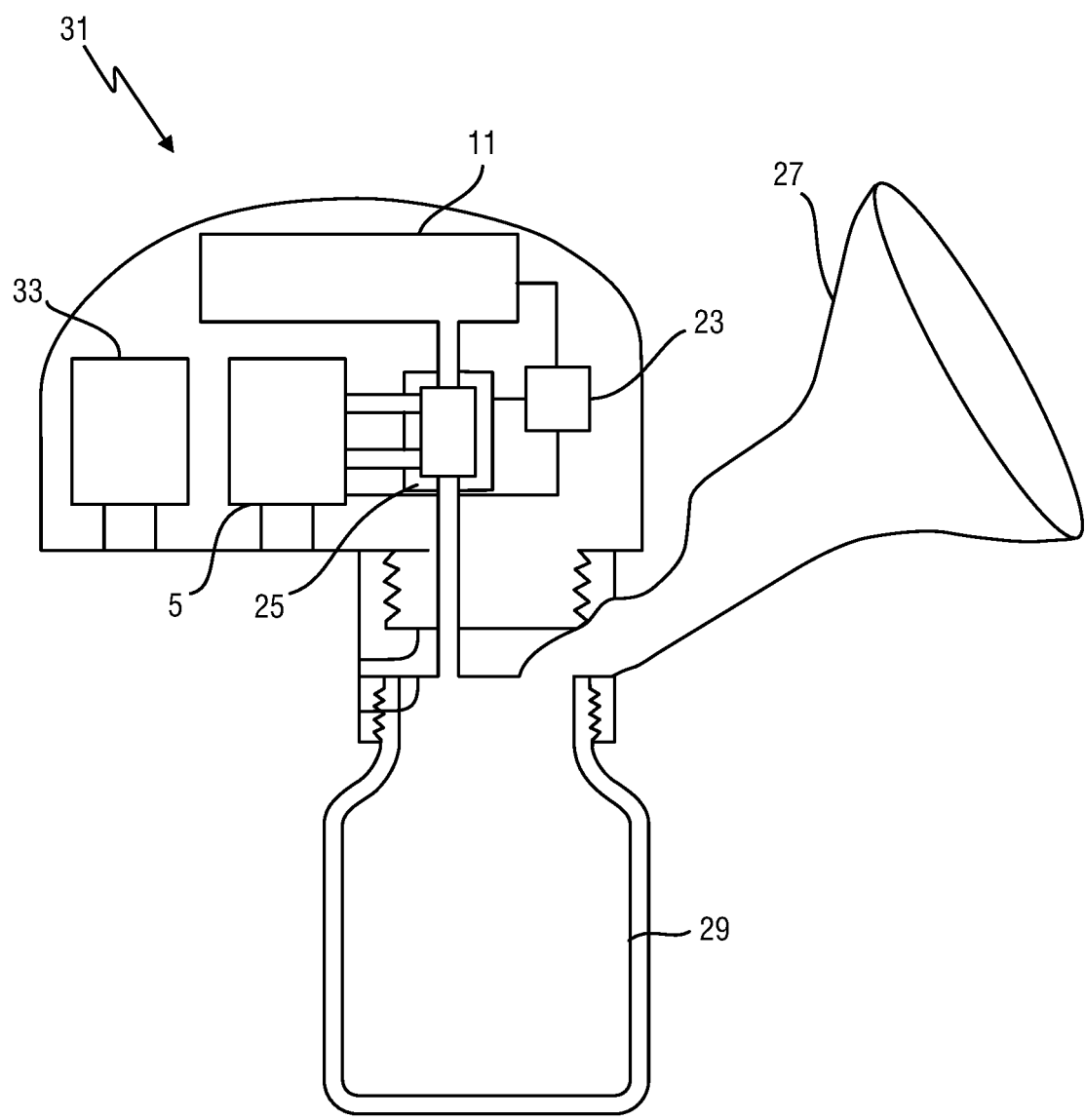
FIG. 7 shows a breast pump device according to an aspect of the present invention.

FIG. 7 illustrates a breast pump device 31 according to another aspect of the present invention. The receiving funnel 27 is shaped to accommodate a breast of a woman. As soon as an underpressure, i.e. a partial vacuum, is applied to the breast, milk is extracted. As illustrated in FIG. 7 the extracted milk is collected in a reservoir 29. This reservoir is evacuated by means of a pump 5 being connected to the reservoir through the smart valve 25. There is further comprised a pressure tank 11 and a controller 23. Further, there is illustrated a battery 33 providing the required electrical energy for the different components. The illustrated smart valve 25 in this embodiment incorporates the functionalities of the directional control valve, the unidirectional valve and the release valve. It also functions as a safety valve preventing harm to the user in case of a malfunctioning pump 5. The controller 23 controls the smart valve 25, measures the pressure in the pressure tank 11 and controls the pump 5.

Although not illustrated, it may also be possible that a mechanical pump is used instead of an electric pump. This would imply that the controller 23 does not need to be connected to the pump 5. A mechanical pump usually comprises a handle for manually exerting a force in order to generate a decrease of pressure. Further, there is usually provided peripheral equipment (not illustrated) such as, e.g., a user interface (e.g. acoustic, visual or mechanical feedback means in combination with buttons, a touchpad, a trackball or other input means), a power source (e.g. a battery, a solar or other energy harvester or a mains-supply connector) or design elements for improving the visual perception of a breast pump.

Alternative to the switching of the pressure tank from the inlet to the outlet of the pump, it is also possible to connect multiple pumps in series, such that the outlet of one pump is directly connected to the inlet of another. This also allows increasing the vacuum level.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. An apparatus for evacuating a collection container, comprising:
   a pump arranged to generate a decrease of pressure between an inlet and an outlet;
   the collection container arranged to store a medium to be transported into an atmosphere through a first flow path;
   a pressure tank arranged to store the medium to be transported from the pressure tank into the atmosphere through a second flow path;
   wherein the pressure tank is arranged to preserve an applied pressure value for a period of time to ensure that the pump evacuates to a deeper vacuum in the collection container than would otherwise be achievable without the assistance of the pressure tank;
   the apparatus further comprising:
   a directional control valve for switching the pressure tank to either the inlet or the outlet of the pump, the pump arranged to transport the medium out of both the collection container and the pressure tank into the atmosphere when the pressure tank is connected to the pump inlet; and
   wherein the directional control valve is configured to switch the pressure tank from the inlet to the outlet of the pump when a predefined criterion is fulfilled.

2. The apparatus according to claim 1, further comprising a unidirectional valve coupled between the outlet of the pump and the pressure tank arranged to prevent a backflow of fluid from the atmosphere into the pump and/or the pressure tank.

3. The apparatus according to claim 2, wherein the directional control valve and the unidirectional valve are combined in a smart valve.

4. The apparatus according to claim 3, wherein the smart valve is fully mechanically controlled.

5. The apparatus according to claim 4, wherein the predefined throughput is a percentage of a maximum throughput that can be realized by the pump.

6. The apparatus according to claim 1, further comprising a sensor arranged to determine a pressure in the pressure tank.

7. The apparatus according to claim 6, wherein the directional control valve is arranged to switch the pressure tank from the inlet to the outlet of the pump when a pressure in the pressure tank is below a predefined pressure threshold.

8. The apparatus according to claim 7, wherein the directional control valve is an electrically operated valve.

9. The apparatus according to claim 8, wherein the directional control valve is arranged configured to switch the pressure tank from the inlet to the outlet of the pump when the throughput of the pump exceeds a predefined throughput threshold.

10. The apparatus according to claim 7, wherein the directional control valve is a mechanically operated valve to allow an operator to manually switch the pressure tank from the inlet to the outlet of the pump.

11. The apparatus according to claim 1, further comprising a sensor arranged to determine a throughput of the pump.

12. The apparatus according to claim 1, further comprising a release valve for releasing a pressure from the collection container and/or the pressure tank to the atmosphere.

13. The apparatus according to claim 1, further comprising a flow restrictor arranged to control a flow of the transported medium from the pressure tank to the outlet of the pump.

14. The apparatus according to claim 1, wherein the pump is one of a positive displacement pump for moving a medium from the pump inlet to the pump outlet.

15. The apparatus according to claim 14, wherein the smart valve is an integrated part combining the functionality of a control valve and unidirectional valve in one component.

16. The apparatus according to claim 1, wherein the pump is an electrical pump controllable by one of a processor or a direct user interface.

17. The apparatus according to claim 16, wherein the smart valve further includes a release valve.

18. The apparatus according to claim 1, wherein the directional control valve is a 3/2 valve having 3 ports and 2 switching positions.

19. The apparatus according to claim 1, wherein the directional control valve is one of an electrically or mechanically operated control valve.

20. The apparatus according to claim 1, further comprising a controller arranged to control the pump and/or the directional control valve.

21. The apparatus according to claim 1, wherein the predefined criterion is a throughput level of the vacuum pump being below a predefined throughput.

22. The apparatus according to claim 1, wherein the predefined criterion is a pressure in the pressure tank being below a predefined pressure threshold, wherein the predefined pressure threshold is dependent on a characteristic of the pump.

23. The apparatus according to claim 1, wherein the predefined criterion is a pressure in the pressure tank being below a predefined pressure threshold, wherein the predefined pressure threshold is dependent on a characteristic of the pump.

24. A breast pump device comprising: an apparatus comprising: a pump coupled to the collection chamber at an inlet of the pump and arranged to generate a decrease of pressure between the inlet and an outlet; the collection container arranged to store a first medium to be transported via the pump into an atmosphere through a first flow path; a pressure tank arranged to preserve an applied pressure value and arranged to store a second medium to be transported from the pressure tank into the atmosphere through a second flow path; wherein the pressure tank is arranged to preserve said applied pressure value for a period of time to ensure that the pump evacuates to a deeper vacuum in the collection container than would otherwise be achievable without the assistance of the pressure tank; the apparatus further comprising: a receiving funnel coupled to the collection chamber for receiving a breast of a woman; and a milk reservoir for collecting milk, a directional control valve for switching the pressure tank to either the inlet or the outlet of the pump, the pump arranged to transport the first medium out of the collection container and the second medium out of the pressure tank into the receiving funnel when the pressure tank is connected to the pump inlet; and wherein the directional control valve is configured to switch the pressure tank from the inlet to the outlet of the pump when a predefined criterion is fulfilled.

25. The breast pump device according to claim 24, wherein the receiving funnel is an exchangeable funnel to accommodate different shaped breasts.

26. The breast pump device according to claim 24, wherein the predefined criterion is a throughput level of the vacuum pump being below a predefined throughput.

* * * * *